US009675248B2

United States Patent
Winsor

(10) Patent No.: US 9,675,248 B2
(45) Date of Patent: Jun. 13, 2017

(54) METHOD AND APPARATUS FOR FIXATION MEASUREMENT AND REFRACTION ERROR MEASUREMENT USING WAVE-FRONT ERROR

(71) Applicant: REBIScan, Inc., Cambridge, MA (US)

(72) Inventor: Robert Scott Winsor, Round Hill, VA (US)

(73) Assignee: REBIScan, Inc., Cambridge, MA (US)

( * ) Notice: Subject to any disclaimer, the term of this patent is extended or adjusted under 35 U.S.C. 154(b) by 0 days.

(21) Appl. No.: 14/978,901

(22) Filed: Dec. 22, 2015

(65) Prior Publication Data

US 2016/0242644 A1 Aug. 25, 2016

Related U.S. Application Data

(60) Provisional application No. 62/118,894, filed on Feb. 20, 2015.

(51) Int. Cl.
*A61B 3/14* (2006.01)
*A61B 3/00* (2006.01)
*A61B 3/103* (2006.01)
*A61B 3/113* (2006.01)
*A61B 3/12* (2006.01)

(52) U.S. Cl.
CPC ............. *A61B 3/14* (2013.01); *A61B 3/103* (2013.01); *A61B 3/113* (2013.01); *A61B 3/12* (2013.01); *A61B 3/0025* (2013.01)

(58) Field of Classification Search
USPC .................................................. 351/200–246
See application file for complete search history.

(56) References Cited

U.S. PATENT DOCUMENTS

| 6,004,313 | A | 12/1999 | Shimmick et al. | |
|---|---|---|---|---|
| 6,550,917 | B1 | 4/2003 | Neal et al. | |
| 8,545,023 | B2 * | 10/2013 | Holladay | A61B 3/1005 351/206 |
| 8,550,624 | B2 * | 10/2013 | Padrick | A61B 3/152 351/200 |
| 8,876,290 | B2 * | 11/2014 | Sarver | A61B 3/0025 351/206 |
| 2005/0225725 | A1 | 10/2005 | Warden et al. | |
| 2006/0023161 | A1 * | 2/2006 | Imaizumi | A61B 3/1035 351/211 |
| 2008/0284979 | A1 | 11/2008 | Yee et al. | |

FOREIGN PATENT DOCUMENTS

| WO | 0128408 A2 | 4/2001 |
|---|---|---|
| WO | 2004010860 A1 | 2/2004 |
| WO | 2011047214 A2 | 4/2011 |

OTHER PUBLICATIONS

International Search Report and Written Opinion cited in corresponding International Application no. PCT/US15/67455 dated Mar. 10, 2016.

* cited by examiner

*Primary Examiner* — Mohammed Hasan
(74) *Attorney, Agent, or Firm* — Amardeep S. Grewal; Reed Smith LLP

(57) ABSTRACT

A method and apparatus for fixation measurement includes projecting, by an image projector, a stimulus onto one or more eyes of a patient via a beam splitter, and capturing, by one or more image sensing devices disposed conjugate to the one or more eyes, a reflected image including light reflected from the one or more eyes in response to the stimulus, the reflected image including information indicating the fixation of the one or more eyes.

16 Claims, 10 Drawing Sheets

METHOD AND APPARATUS FOR FIXATION MEASUREMENT AND REFRACTION ERROR MEASUREMENT USING WAVE-FRONT ERROR

RELATED APPLICATION DATA

This application claims priority to U.S. Provisional Application No. 62/118,894, filed Feb. 20, 2015, the disclosure of which is hereby incorporated by reference in its entirety.

BACKGROUND

Within the field of optometry, there exist many devices that are used to assess the direction of fixation of an eye. An example of such a device is described in U.S. Pat. No. 6,027,216, the contents of which are hereby incorporated in their entirety. Many such devices utilize either a scanning laser beam to perform measurements or rely on measurements using polarized light sources.

Methods of scanning a laser beam to perform measurements typically involve the mechanical movement of an optical device. For retinal birefringence scanning, there is a mirror that is both tilted and spinning at a high speed (e.g. 12,000 rpm). When utilizing mechanical movements of optical devices, vibrations can present significant complexities to scanning instruments. The vibrations must be kept low enough so as not to impact the measurements intended by the instrument.

There are other complications with using mechanical movements for scanning optical instruments, such as:

Lifetime of the assembly—motors have a shorter life span than virtually all other components.

Fabrication—tight tolerances are required to achieve balance.

Assembly—highly skilled personnel are required to assemble the mechanism and make adjustments to minimize vibrations: this is unlikely to be an automated process.

Noise—even relatively quiet motors will make an audible sound that can be distracting to a patient.

Safety—the failure of a component spinning at 12,000 rpm can pose significant risk to the rest of the instrument if there is a failure of part of the mechanism (due to issues such as fatigue).

Cost—the combination of the above issues generates significant requirements on the design of the instrument that add time and materials to the production process, increasing overall cost.

Furthermore, methods of measuring fixation that use polarization techniques depend heavily on measurements of relative intensity of light. The measurement of a change in polarization is ultimately reduced to a change in intensity of light—the change in the polarization state is measured and estimated proportional to the intensity of the measured signal. Such changes in light intensity must be measured in the environment containing very low background light in order for the result to be accurate. In practice, the signal-to-noise ratio requirements for polarization measurements of signals reflecting from the retina can be challenging to meet.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

The inventors have identified a need for a system which measures fixation and which does not depend on polarization techniques or require any scanning mechanisms.

Many of the problems associated with the scanning method can be reduced by altering the method of sensing, and transitioning the design to the use of an imager to capture, within a single image, the entire information required to determine fixation.

Figure 1A:
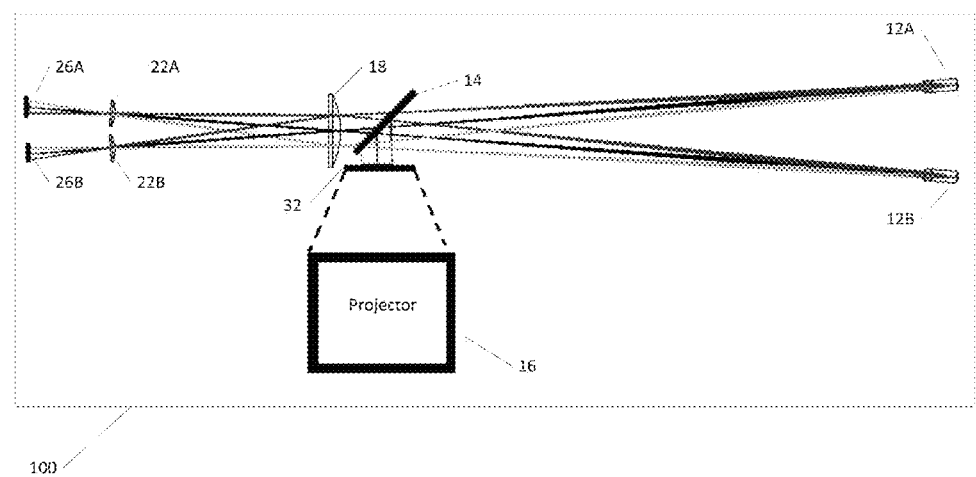
FIGS. 1A-1B illustrate apparatuses for fixation measurement according to an exemplary embodiment.

FIG. 1A illustrates an apparatus 100 for fixation measurement according to an exemplary embodiment. As shown in FIG. 1A, the apparatus 100 includes a beam splitter 14, a projection system 16, a convex lens 18, focusing lenses 22A and 22B, and image sensing devices 26A and 26B. As will be described in greater detail below, apparatus 100 utilizes an image-based scanning method to measure fixation. By using an image-based scanning method, the above-described components of the apparatus 100 may be fixed in place—they do not need to move or rotate. Additionally, as described below, the image-based scanning method of the present application does not rely on measurements of polarized light and therefore does not require that the surrounding environment have very low background light.

The beam splitter 14 can be any suitable type of beam splitter. The projection system 16 is configured to generate a stimulus and project the generated stimulus to a projection plane 32 which is positioned below the beam splitter 14. Since this stimulus is the target fixation point for the patient who is being examined, the stimulus can also be referred to as the target. As discussed further below, the target (stimulus) used in the present system can be in the form of a variety of shapes, such as concentric circles or a grid of double lines.

Figure 7:
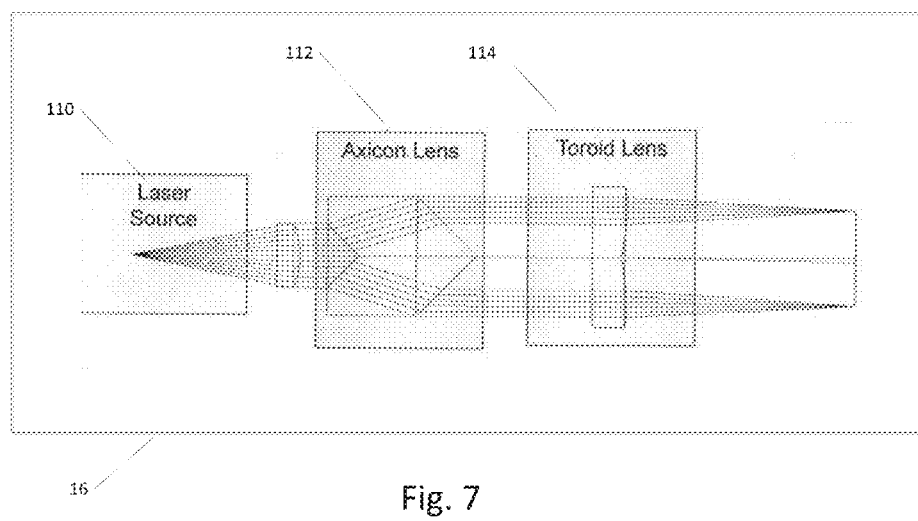
FIG. 7 illustrates an image projection system according to an exemplary embodiment.

The projection system 16 can be any type of stimulus projection system. For example, as shown in FIG. 7, the projection system 16 can include a laser source, an axicon lens and a toroid lens which are utilized to generate and/or project the target. As shown in FIG. 7, the projection system 16 can include a laser source 110, an axicon lens 112 and a toroidal lens 114. By utilizing the axicon lens 112 in concert with the toroidal lens 114, a round target can be generated without the need for a rotating mirror. When using this projection system, the optics are rotationally symmetric.

Additionally or alternatively, the projection system 16 can include a holographic device which is utilized to generate and/or project the target. The projection system 16 can also include diffuse media in lieu of lenses.

Figure 8:
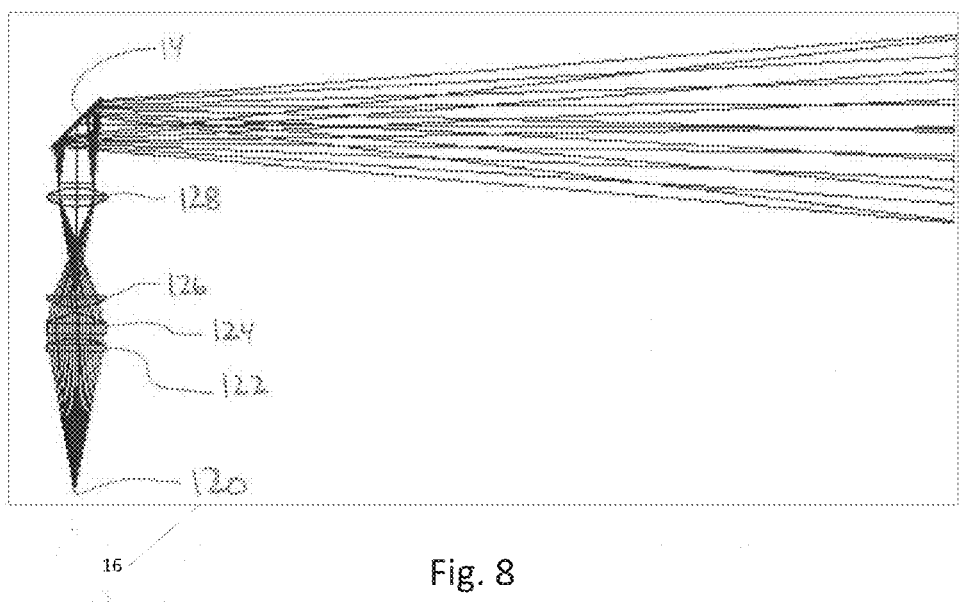
FIG. 8 illustrates another image projection system according to an exemplary embodiment.

Additionally, as shown in FIG. 8, the projection system 16 can include a light source (e.g., a diode laser), a first plano-convex lens, an axicon lens and a second plano-convex lens. As shown in FIG. 8, the projection system 16 includes a light source 120, a first plano-convex lens 122, an axicon lens 124 and a second plano-convex lens 126. The light source 120 may be any suitable type of light source. For example, the light source 120 can be a diode laser. The axicon lens 124 is positioned between the first and second plano-convex lenses 122, 126. When using this projection system, the target is immersed in the bi-convex lens 128, but the appearance of the target from the perspective of the patient will be "behind" the beamsplitter 14.

Referring back to FIG. 1A, the convex lens 18 may be any suitable type of convex lens and operates as a pupil reimaging lens. The focusing lenses 22A and 22B can be any suitable type of convex lenses, and can be selected based on the types of image analysis to be performed. Focusing lens 22A is associated with a first eye 12A of a person (such as a patient) and focusing lens 22B is associated with a second eye 12B of the person.

The image sensing devices 26A and 26B cay be any suitable type of image sensing device. For example, according to various embodiments, the image sensing devices 26A and 26B can be charge coupled device (CCD) image sensors, complementary metal—oxide—semiconductor (CMOS) image sensors, etc. The image sensing devices 26A and 26B can be selected based on the desired image size and the focal length of the second and third convex lenses 22A and 22B. The first image sensing device 26A is associated with a first eye 12A of the person and the second image sensing device is associated with a second eye 12B of the person. The image sensing devices 26A and 26B can be utilized to capture, with a single image, the entire information contained from a single scan.

The apparatus 100 can also be configured so that light reflected from both of the eyes 12A and 12B meets at a single convex lens and is imaged onto a single image sensing device. In this case, focusing lenses 22A and 22B can be replaced by a single convex lens and image sensing devices 26A and 26B can be replaced by a single image sensing device.

In operation, the projection system 16 utilizes laser light to generate the target, and the projection system projects the target to the projection plane 32. When a person (hereinafter referred to as a patient) positions his or her eyes 12A and 12B to look into the apparatus 100 and at the target (which appears to the patient to be in a direct line of sight), light representative of the target is instantaneously imaged onto the patient's eyes 12A and 12B (onto the retinas of the eyes).

Light representative of the target enters the patient's eyes 12A and 12B and a portion of this light is reflected off the fundus of each eye. The reflected light passes back out the patient's eyes 12A and 12B, through the beam splitter 14, through the first convex lens 18, through the focusing lenses 22A and 22B and onto the image sensing devices 26A and 26B, which are conjugate to the patient's retinas. The convex lens 18 operates to converge the light onto the focusing lenses 22A and 22B. The specific position of the focusing lenses 22A and 22B can be determined by the requirements of the apparatus 100, such as overall size, allowable sensor locations, etc. The focusing lenses 22A and 22B can be considered exit pupils, and operate to focus the light onto the image sensing devices 26A and 26B, which then capture the reflected target image.

Figure 1B:
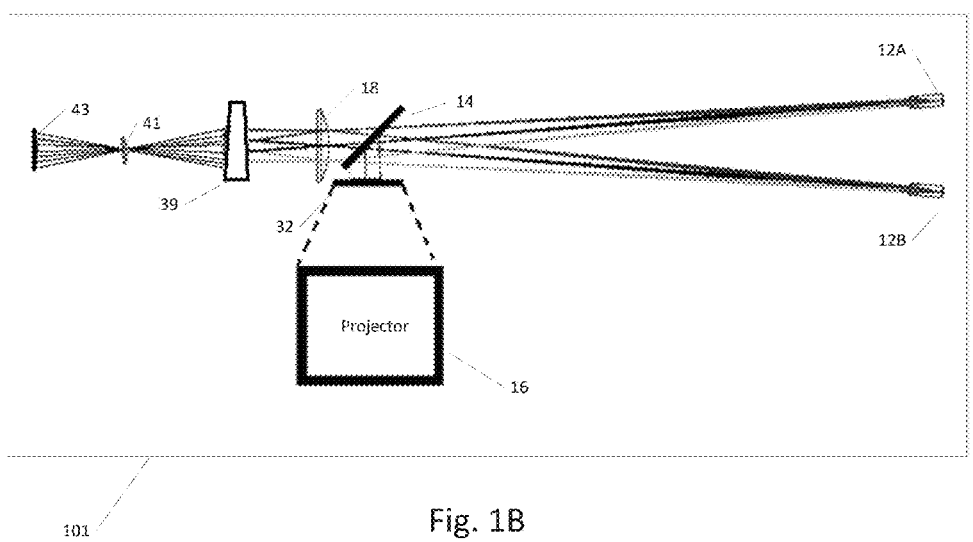

The apparatus 100 can also be configured so that light reflected from both of the eyes 12A and 12B meets at a single convex lens and is imaged onto a single image sensing device. An example of this is shown in apparatus 101 of FIG. 1B, which is similar to the apparatus 100 of FIG. 1A, except that focusing lenses 22A and 22B are replaced by a single convex lens 41, image sensing devices 26A and 26B are replaced by a single image sensing device 43, and prism 39 is added to focus reflected light onto lens 41.

Figure 2:
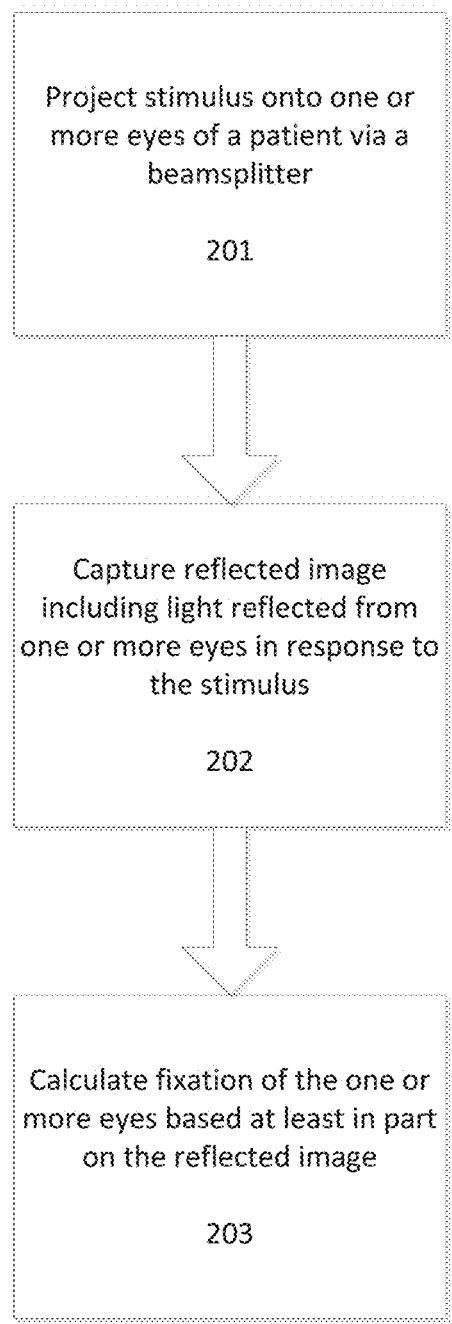
FIG. 2 illustrates a flowchart for fixation measurement according to an exemplary embodiment.

FIG. 2 illustrates a flowchart for a method of fixation measurement according to an exemplary embodiment. The method, or steps in the method, can be performed using an apparatus such as the one described with reference to FIG. 1A or FIG. 1B.

At step 201 a stimulus (target) is projected onto one or more eyes of a patient via a beam splitter. The stimulus can be projected by an image projection system as described earlier. For example, a stimulus can be generated using unpolarized laser light to create the appearance of a grid of double lines, hereinafter referred to as the target. The target can a double grid to provide closely spaced sets of lines. The proximity of the lines can be chosen such that a well-focused eye will resolve both lines, but a partial defocus (of, for example ⅛ diopter) will result in the lines being blurred together.

Figure 3:
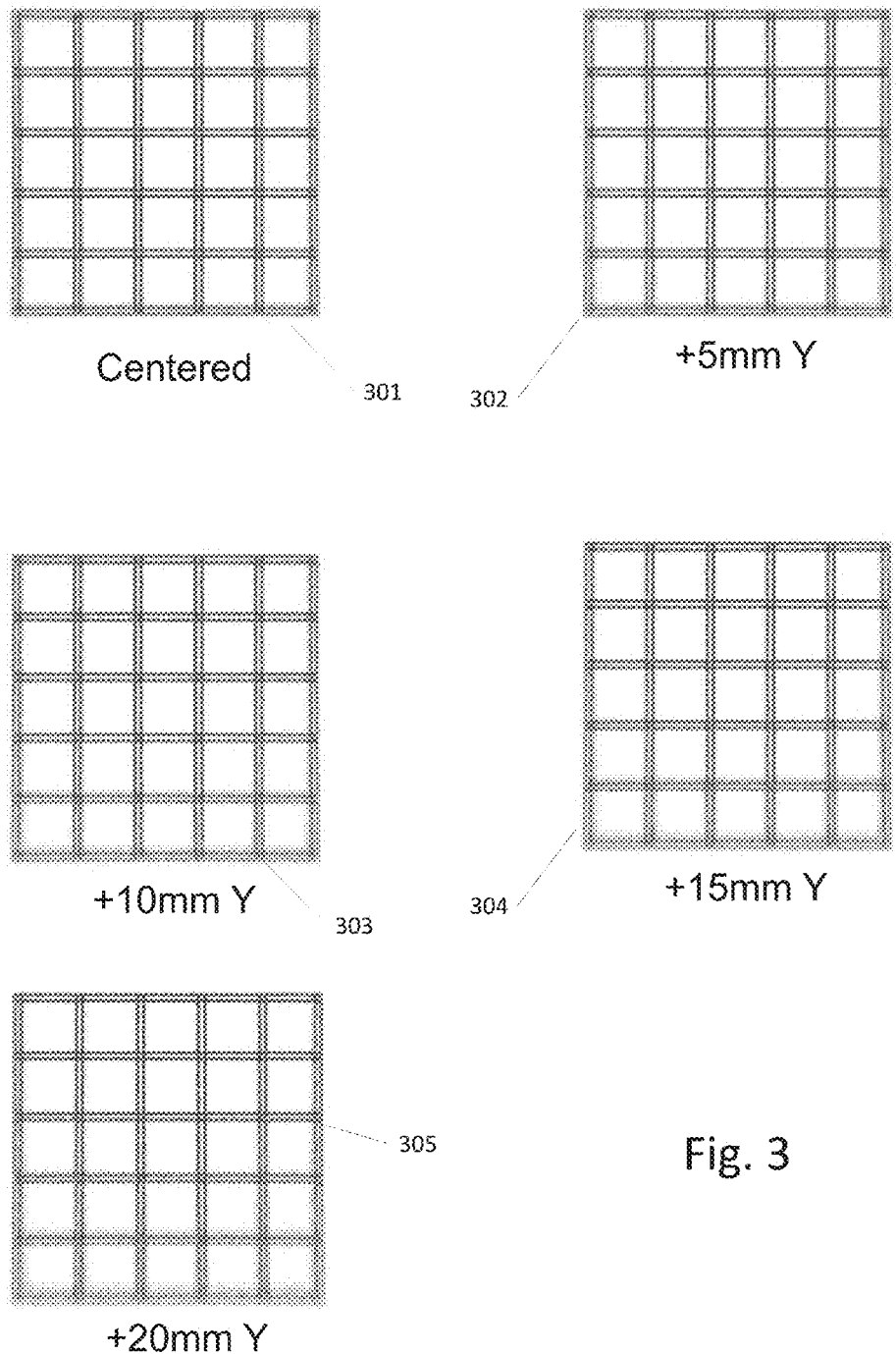
FIG. 3 illustrates a simulation of target images as perceived by an eye varying according to different fixation points of the eye.

For example, FIG. 3 illustrates a target comprising a grid of double lines as perceived on a retina. The target size can vary depending on the apparatus and the patient. For example, the size of the target can be 50 mm at a 300 mm range. When the fixation of the eyes is centered, as shown in image 301, all of the double lines in the grid are resolved and distinguishable. However, when the eyes are fixated on progressively higher points above the center point, as shown in images 302, 303, 304, and 305, part of the double lines on the opposite of the grid become blurred together, indicating a partial defocus on that region of the grid.

At step 202 a reflected image including light reflected from the one or more eyes in response to the stimulus is captured by one or more image sensing devices disposed conjugate to the one or more eyes. This reflected image includes information indicating the fixation of the one or more eyes. As discussed above, the nature of the optics of the eye is such that when a target is well-focused on the center of the macula, there is a distance from the center at which the target degrades from being well focused and becomes out of focus (this is a result of wavefront error). Therefore, using a double-grid set of lines, a patient looking at the target with proper focus will reveal a central region of the re-imaged target that has resolved line pairs. However, off axis, the line pairs will become smeared and rather than being resolved as two lines, they will be resolved as one line. The location of the fixation of the one or more eyes can then be determined based on how far off-center the lines are resolved.

Figure 4:
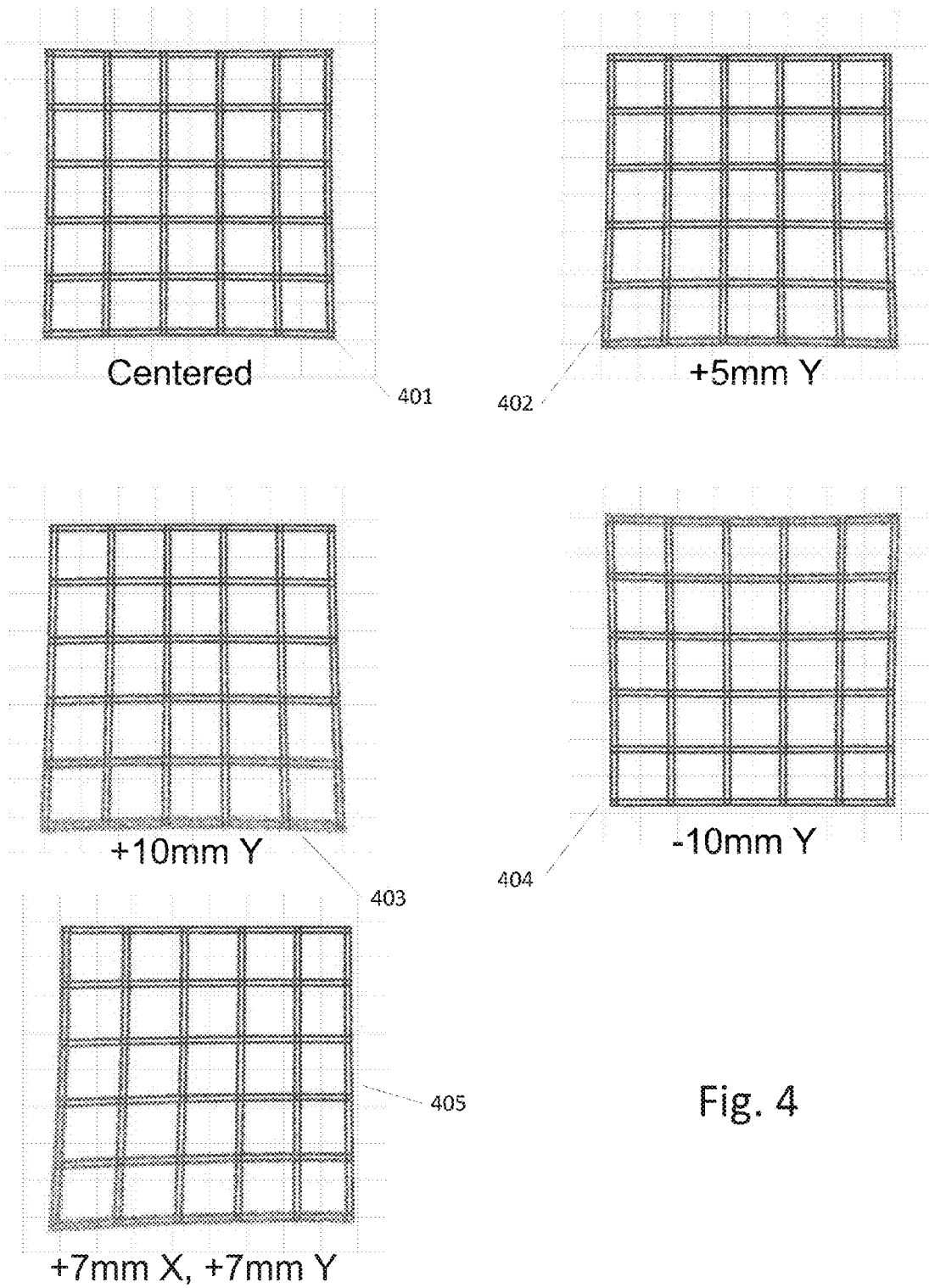
FIG. 4 illustrates reflected target images captured from an eye varying according to different fixation points of the eye.

FIG. 4 illustrates examples of the reflected image captured by the one or more image sensing devices. Image 401 indicates a fixation point in the center of the grid. Images 402 and 403 indicate progressively higher fixation points of +5 mm Y and +10 mm Y. This is reflected in the blurriness of the double lines on the opposite side of the grid.

The size of the targets in FIGS. 3 and 4 are different to highlight some optical differences, especially to show that the errors generated by a single-pass through the eye (FIG. 3) are smaller and less noticeable than the errors generated by a double-pass through the eye (FIG. 4).

At step 203, a fixation of the one or more eyes is calculated by one or more computing devices based at least in part on the reflected image. As discussed above, the fixation of the one or more eyes can be calculated based at least in part on one or more locations of relative line-blur in the reflected image. For example, an algorithm could be used to identify all of the locations (coordinates) of line blur and then calculate a probable fixation point of the eyes based on the locations of line blur.

Additionally, there is another aspect to the reimaged target that can be analyzed to determine fixation, and this is grid distortion. Due to the lens shapes of the various components in the eye (the anterior and posterior surfaces of the cornea, the lens), and the curvature of the retina, the reimaged target will not be imaged as a true grid of straight lines. Rather, the lines will be reimaged with slight curvature to them. Each point on the lines will be reimaged such that the further the point is from the center of the optical axis of the eye, the further the point will be dislocated off-axis when it is reimaged. For example, a simple square box being viewed by a well fixated eye would have a reimaged box with sides that are pushed in toward the center (or corners that are pulled further outward from center). This type of optical distortion is commonly called pincushion, and can also be thought of as field-dependent magnification: the further off-axis, the greater the magnification. This effect can be seen in the images in FIG. 4, which display the pincushion effect, resulting in a curvature of sides of the grid depending on the point of fixation of the one or more eyes.

Due to the curvature of the reimaged grid, it is possible through the use of image processing to evaluate the reimaged lines and determine the location of fixation within the grid—or in the case of a patient that is not fixated properly on the target, to determine that fixation is outside the grid (and therefore not fixating on-center).

Whether using distortion or the blur of the set of lines to determine fixation, it is important to note that the eye does not necessarily need to be well-focused to measure fixation. If the image has a region where the lines are resolved, it helps with image processing. However even if the eyes are not focused well, there will still be a measureable change in the blur of the line pairs. Depending on which side of focus the patient may be (myopic or hyperopic), the general pattern will be that there is a roughly circular region where the focus is best. If a full circle of best focus can be measured and the center of that circle is sufficiently close to the center of the grid, then the eye has demonstrated fixation. For distortion, the approximate magnification across the grid can be utilized, with a similar circular arrangement of values on the grid (having a center sufficiently close to the center of the grid) being an indication of fixation for the eye. A successful measurement—in each eye simultaneously—indicates passing the test for fixation.

A benefit of using an image-based approach is the ability to choose the integration time for the image exposure. The time of the exposure ideally should be as short as possible to minimize the effects of background signals. The shorter the integration time, the less background light that will be measured. By having the entire visual stimulus (of the double-grid, for example) be imaged at once, it is possible to have the illumination be performed with a pulsed laser. The pulse can be substantially bright enough to provide significant signal during even very short integration times. This allows for a means to achieve very high signal to noise ratio, improving the image processing algorithm accuracy. The shorter exposure time also permits a better sampling of the retina during a scan, as it greatly reduces the amount of movement that is possible during a sampling interval. Compared with a scanning technique operating at 200 Hz, which would require 5 ms to achieve a single revolution scan (and multiple scanner rotations are required to establish the frequencies that need to be measured), an image can be captured in much less than a millisecond (for example, 10 us) and all the information is contained within that single image Aside from alleviating the problems associated with polarization and mechanical scanning, there are many additional benefits of the disclosed apparatus and method.

Images can be stored, and these are likely to offer clinical benefits as the patient ages. Any changes as a function of age would not be limited to a "pass" or "fail". An ophthalmologist would have an opportunity to review the images and determine if there is any other useful information. For example, the magnitude of the fixation error can be estimated.

Images can be analyzed to determine the nature of the stray light, possibly allowing further investigation into methods of reducing noise.

The imagers used to determine fixation are likely to be very useful to measure other optical characteristics of the eyes, given the appropriate design. Most notable is the desire to measure refraction error in each eye, such as astigmatism, nearsightedness, or farsightedness.

Using an imager-based method of measuring birefringence fixation allows image-based methods of also performing refraction error measurements.

As mentioned above, a significant benefit to using image based measurements for fixation measurements is the ability to repurpose the image sensors to measure refraction errors. Although the methodology for measuring refraction is somewhat different than what is required for measuring fixation, the lenses and image sensors can be designed to be common to both use cases. This offers a benefit to a medical professional because it reduces the number of instruments that are needed to achieve a full examination of the patient, whether the medical professional is a pediatrician or an ophthalmologist.

Figure 5:
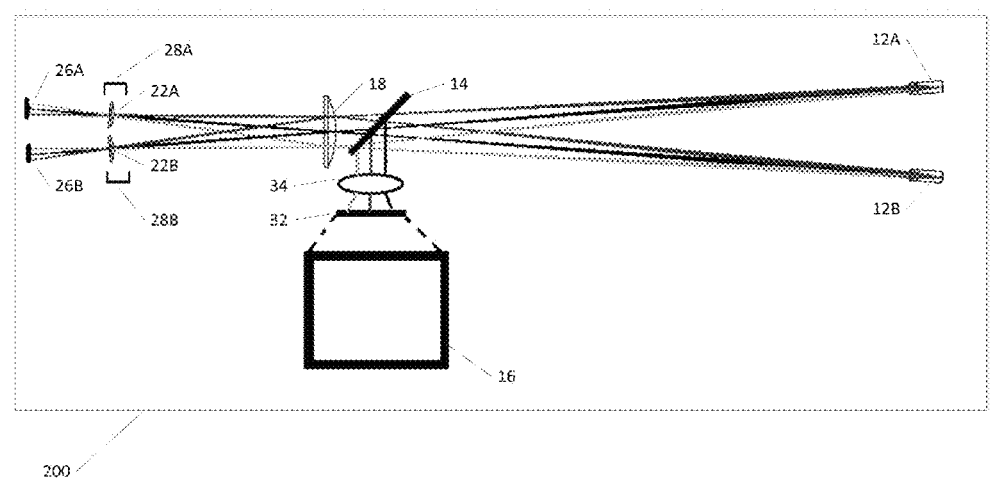
FIG. 5 illustrates an apparatus for refractive error measurement according to an exemplary embodiment.

An apparatus for measurement of refractive error is shown in FIG. 5. Many of the components shown in FIG. 5 are similar to those of the apparatus of FIG. 1A, including image projection system 16, beam splitter 14, convex lens 18, focusing lenses 22A and 22B, and image sensing devices 26A and 26B. The focusing lenses 22A and 22B and image sensing devices are also associated with one or more eyes of patient 12A and 12B.

The nominal range for retinal birefringence scanning is 400 mm, or 2.5 diopters. A typical patient would be accommodating to the target at this range. This would not sufficiently test a patients' ability to adjust refraction to accommodate objects at other distances. Therefore, an additional lens 34 can be added to the instrument between the viewing target and the patients' eyes 12A and 12B. This lens 34 can be positioned into place by the medical professional performing the refraction measurement (for example, by means of a cartridge that is pushed into place for the refraction measurement, but pulled out of place for the fixation measurement). The lens 34 can have a focal length and be positioned such that it is at a distance from the target to make the target appear as if it is located many meters in range (nominally less than $1/10^{th}$ diopter) and further away than it actually is.

During measurement of refraction, the image sensing devices 26A and 26B can capture images while the focusing lenses 22A and 22B that lie immediately in front of the image sensing devices 26A and 26B can be adjusted for focus. The focusing lenses 22A and 22B can be configured to be displaced along an axis by a focusing mechanism (not shown) to thereby alter the one or more reflected images captured by the one or more image sensing devices. For example, as shown in FIG. 5, focusing lens 22A can be displaced along the range shown by 28A and focusing lens 22B can displaced along the range shown by 28B.

The focus mechanism can be manufactured such that changes in the displacement of each focusing lens are well-correlated with known levels of refraction error. One common way to achieve this is to simply measure the position of the focus mechanism in microns. The number of microns that the focus mechanism is shifted from the nominal (no refractive error) position tells the amount of refraction error that is being measured. Therefore, based on the position of the focus mechanism that is required to achieve the best conjugate image of the retina, the patients' spherical refraction error can be measured.

Figure 6:
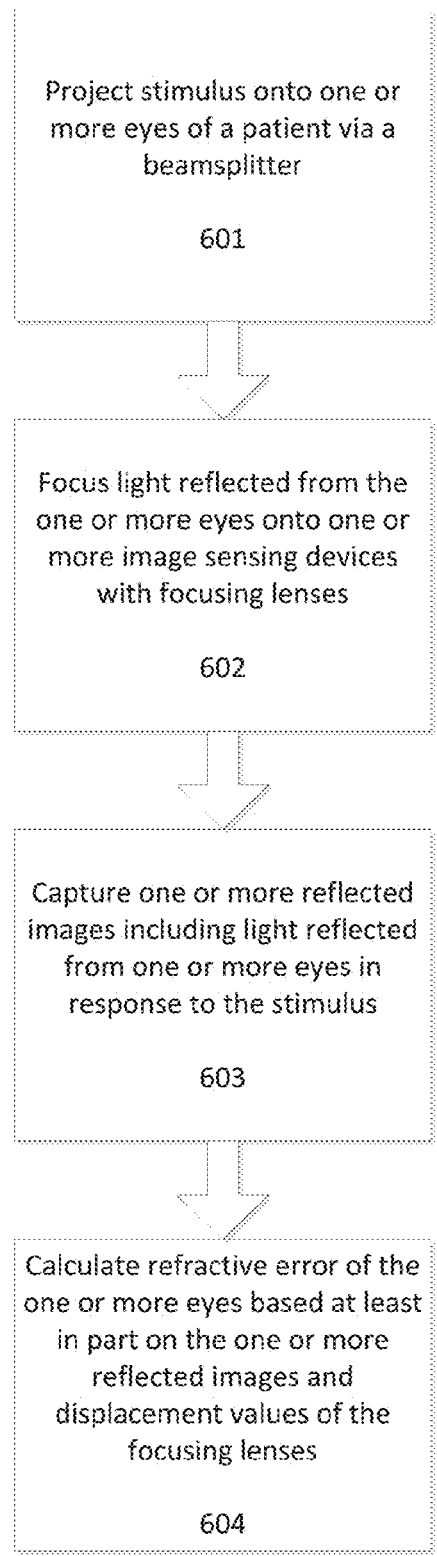
FIG. 6 illustrates a flowchart for refractive error measurement according to an exemplary embodiment.

FIG. 6 illustrates a flowchart for a method of refractive error measurement according to an exemplary embodiment. The method, or steps in the method, can be performed using an apparatus such as the one described with reference to FIG. 5.

At step 601 a stimulus (target) is projected by an image projection system onto one or more eyes of a patient via a beam splitter. A lens can be disposed between the stimulus and the one or more eyes which has a focal length and position relative to the stimulus (target) such that the stimulus (target) appears to the patient to be further away than it is.

To measure astigmatism, the target being imaged would preferentially have features that would assist in the determination of this type of error. One example target would be comprised of a series of pairs of short lines, spaced every 3 degrees. An example of this type of target is similar to a watch dial, although rather than each minute marker being just one line, it would consist of a double line. The angular diameter of this "watch dial" target would nominally be approximately the same diameter as that used for measuring fixation error, or about 3 degrees (1.5 degrees from center to edge). The series of double lines in this manner would appear during an exam as being entirely in-focus at a particular focus setting for a patient with no astigmatism. However, if the patient has astigmatism, there will be regions where the double-lines will smear due to the astigmatism error. The location of the lines that smear will also indicate the axis of the astigmatism error. As the focus mechanism is adjusted (preferentially using an automated procedure), the location of the double-lines that are in focus and out of focus will shift for a patient that has astigmatism. There will be a focus position that provides best sharpness for some lines, while the others are out of focus. Further adjustment of the focus mechanism will alter this, however, and the lines that were previously smeared will become sharply focused. Additionally, the lines that were previously well focused will then become smeared (nominally the groups of lines that are in best focus and those with the most smear will be at 90 degrees to each other). Measuring the focus shift required to achieve best focus for all of these lines will tell the magnitude of the astigmatism, whereas the midpoint between these (the position at which virtually all sets of line will be similarly smeared) will be the average refraction error.

Another method is to simply use two concentric rings, closely spaced. A patient with astigmatism will exhibit images with the rings resolved in two locations, directly opposite of each other with respect to the center of the ring. The remaining sections of the ring will be smeared. As focus is shifted, the regions where the ring is optimally resolved will shift roughly 90 degrees. By recording the shift in focus between these two cases, the astigmatism refraction error can be measured, as can the axis of the error as determined by the locations where the ring is resolved as focus is changed. An image target comprised of a double ring is preferable due to its ability to be used for both fixation and refraction measurements.

At step 602 one or more focusing lenses disposed between one or more image sensing devices and the one or more eyes are used to focus the light reflected from the one or more eyes onto the one or more image sensing devices. As discussed above, the one or more focusing lenses are configured to be displaced along an axis by one or more focusing mechanisms to thereby alter one or more reflected images captured by the one or more image sensing devices. The displacement of each of the focusing lenses can be recorded, stored, or otherwise tracked as displacement values.

At step 603 one or more image sensing devices disposed conjugate to the one or more eyes capture the one or more reflected images including light reflected from the one or more eyes in response to the stimulus (target).

At step 604 the refractive error in at least one of the one or more eyes is calculated by one or more computing devices based at least in part on the one or more reflected images and one or more displacement values of at least one of the one or more focusing lenses. Each of the one or more displacement values can correspond to a different reflected image in the one or more reflected images. As discussed earlier, the displacement amount corresponding to the reflected image which best resolves the target image can be used to determine the refractive error in an eye (such as by correlating the displacement amount with known levels of refractive error).

Figure 9:
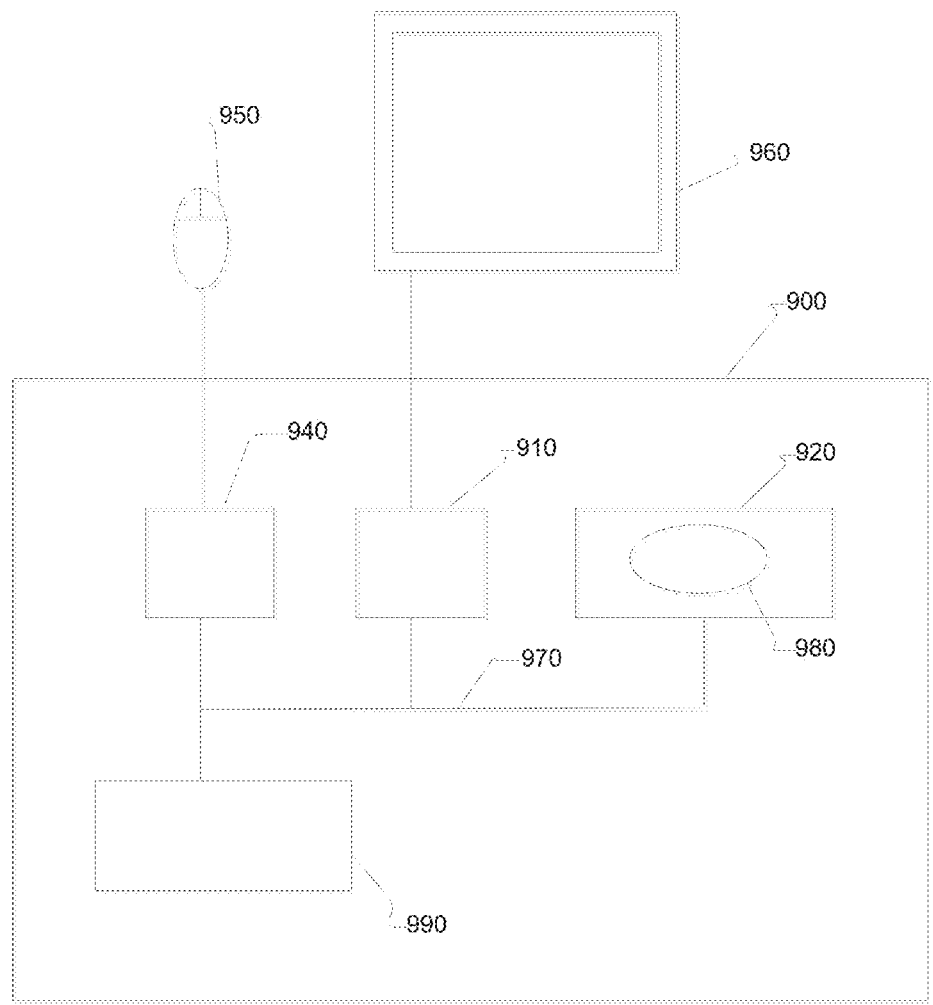
FIG. 9 illustrates an exemplary computing environment that can be used to carry out at least part of the method disclosed herein.

One or more of the above-described techniques can be implemented in or involve one or more computer systems. FIG. 9 illustrates a generalized example of a computing environment 900. The computing environment 900 is not intended to suggest any limitation as to scope of use or functionality of a described embodiment.

With reference to FIG. 9, the computing environment 900 includes at least one processing unit 910 and memory 920. The processing unit 910 executes computer-executable instructions and may be a real or a virtual processor. In a multi-processing system, multiple processing units execute computer-executable instructions to increase processing power. The memory 920 may be volatile memory (e.g., registers, cache, RAM), non-volatile memory (e.g., ROM, EEPROM, flash memory, etc.), or some combination of the two. The memory 920 may store software instructions 980 for implementing the described techniques when executed by one or more processors. Memory 920 can be one memory device or multiple memory devices.

A computing environment may have additional features. For example, the computing environment 900 includes storage 940, one or more input devices 950, one or more output devices 960, and one or more communication connections 990. An interconnection mechanism 970, such as a bus, controller, or network interconnects the components of the computing environment 900. Typically, operating system software or firmware (not shown) provides an operating environment for other software executing in the computing environment 900, and coordinates activities of the components of the computing environment 900.

The storage 940 may be removable or non-removable, and includes magnetic disks, magnetic tapes or cassettes, CD-ROMs, CD-RWs, DVDs, or any other medium which can be used to store information and which can be accessed within the computing environment 900. The storage 940 may store instructions for the software 980.

The input device(s) 950 may be a touch input device such as a keyboard, mouse, pen, trackball, touch screen, or game controller, a voice input device, a scanning device, a digital camera, remote control, or another device that provides input to the computing environment 900. The output device(s) 960 may be a display, television, monitor, printer, speaker, or another device that provides output from the computing environment 900.

The communication connection(s) 990 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations can be described in the general context of computer-readable media. Computer-readable media are any available media that can be accessed within a computing environment. By way of example, and not limitation, within the computing environment 900, computer-readable media include memory 920, storage 940, communication media, and combinations of any of the above.

Of course, FIG. 9 illustrates computing environment 900, display device 960, and input device 950 as separate devices for ease of identification only. Computing environment 900, display device 960, and input device 950 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). Computing environment 900 may be a set-top box, mobile device, personal computer, or one or more servers, for example a farm of networked servers, a clustered server environment, or a cloud network of computing devices.

Having described and illustrated the principles of our invention with reference to the described embodiment, it will be recognized that the described embodiment can be modified in arrangement and detail without departing from such principles. It should be understood that the programs, processes, or methods described herein are not related or limited to any particular type of computing environment, unless indicated otherwise. Various types of general purpose or specialized computing environments may be used with or perform operations in accordance with the teachings described herein. Elements of the described embodiment shown in software may be implemented in hardware and vice versa.

What is claimed is:

1. An apparatus for fixation measurement, the apparatus comprising:
   an image projector configured to project a stimulus onto one or more eyes of a patient via a beam splitter, wherein the stimulus is projected onto one or more retinas of the one or more eyes of the patient; and
   one or more image sensing devices disposed conjugate to the one or more retinas, wherein the one or more image sensing devices are configured to capture a reflected image including light reflected from the one or more retinas in response to the stimulus, wherein the reflected image includes a reflected stimulus comprising one or more of: the stimulus as perceived on the one or more retinas or the stimulus as transformed by a curvature of the one or more retinas, and wherein differences between the stimulus and the reflected stimulus indicate a fixation of the one or more eyes.

2. The apparatus of claim 1, further comprising:
   one or more computing devices configured to calculate fixation of the one or more eyes based at least in part on the stimulus and the reflected stimulus.

3. The apparatus of claim 2, wherein the stimulus comprises a grid of closely-spaced double lines and wherein a distance between the double lines is such that a well-focused eye will resolve both lines but a partial defocus will result in the lines being blurred together.

4. The apparatus of claim 3, wherein the fixation of the one or more eyes is calculated based at least in part on one or more locations of relative line-blur in the reflected stimulus.

5. The apparatus of claim 3, wherein fixation of the one or more eyes is calculated based at least in part on grid distortion in the reflected stimulus.

6. A method for fixation measurement, the method comprising:
   projecting, by an image projector, a stimulus onto one or more eyes of a patient via a beam splitter, wherein the stimulus is projected onto one or more retinas of the one or more eyes of the patient; and
   capturing, by one or more image sensing devices disposed conjugate to the one or more retinas, a reflected image including light reflected from the one or more retinas in response to the stimulus, wherein the reflected image includes a reflected stimulus comprising one or more of: the stimulus as perceived on the one or more retinas or the stimulus as transformed by a curvature of the one or more retinas, and wherein differences between the stimulus and the reflected stimulus indicate a fixation of the one or more eyes.

7. The method of claim 6, further comprising:
   calculating, by at least one or more computing devices, fixation of the one or more eyes based at least in part on the reflected stimulus.

8. The method of claim 7, wherein the stimulus comprises a grid of closely-spaced double lines and wherein a distance between the double lines is such that a well-focused eye will resolve both lines but a partial defocus will result in the lines being blurred together.

9. The method of claim 8, wherein the fixation of the one or more eyes is calculated based at least in part on one or more locations of relative line-blur in the reflected stimulus.

10. The method of claim 8, wherein the fixation of the one or more eyes is calculated based at least in part on grid distortion in the reflected stimulus.

11. An apparatus for measurement of refractive error, the apparatus comprising:
    an image projector configured to project a stimulus onto one or more retinas of one or more eyes of a patient via a beam splitter;
    a lens disposed between the stimulus and the one or more eyes, the lens having a focal length and position relative to the stimulus such that the stimulus appears to the patient to be further away than it is;

one or more image sensing devices disposed conjugate to the one or more retinas, wherein the one or more image sensing devices are configured to capture one or more reflected images including light reflected from the one or more retinas in response to the stimulus; and one or more focusing lenses disposed between the one or more image sensing devices and the one or more eyes, wherein the one or more focusing lenses are configured to focus the light reflected from the one or more retinas onto the one or more image sensing devices, wherein the one or more focusing lenses are configured to be displaced along an axis to thereby alter the one or more reflected images captured by the one or more image sensing devices and wherein the one or more reflected images include a reflected stimulus comprising the stimulus as perceived on the one or more retinas and subsequently focused by the one or more focusing lenses.

12. The apparatus of claim 11, further comprising:
one or more computing devices configured to calculate refractive error in at least one of the one or more eyes based at least in part on the one or more reflected images and one or more displacement values of at least one of the one or more focusing lenses, wherein each of the one or more displacement values corresponds to a reflected image in the one or more reflected images.

13. The apparatus of claim 12, wherein the stimulus comprises two rings and wherein a distance between the two rings is such that a well-focused eye will resolve two lines at the point of focus but a partial defocus will result in the lines being blurred together.

14. A method for measurement of refractive error, the method comprising:
projecting, by an image projector, a stimulus onto one or more retinas of one or more eyes of a patient via a beam splitter, wherein a lens disposed between the stimulus and the one or more eyes has a focal length and position relative to the stimulus such that the stimulus appears to the patient to be further away than it is;

focusing, by one or more focusing lenses disposed between one or more image sensing devices and the one or more eyes, light reflected from the one or more retinas onto the one or more image sensing devices, wherein the one or more focusing lenses are configured to be displaced along an axis to thereby alter one or more reflected images captured by the one or more image sensing devices and wherein the one or more image sensing devices are disposed conjugate to the one or more retinas; and capturing, by the one or more image sensing devices disposed conjugate to the one or more retinas, the one or more reflected images including light reflected from the one or more retinas in response to the stimulus, wherein the one or more reflected images include a reflected stimulus comprising the stimulus as perceived on the one or more retinas and subsequently focused by the one or more focusing lenses.

15. The method of claim 14, further comprising:
calculating, by at least one of the one or more computing devices, refractive error in at least one of the one or more eyes based at least in part on the one or more reflected images and one or more displacement values of at least one of the one or more focusing lenses, wherein each of the one or more displacement values corresponds to a reflected image in the one or more reflected images.

16. The method of claim 15, wherein the stimulus comprises two rings and wherein a distance between the two rings is such that a well-focused eye will resolve two lines at a point of focus but a partial defocus will result in the lines being blurred together.

* * * * *